United States Patent [19]

Harrison et al.

[11] Patent Number: 5,403,326
[45] Date of Patent: Apr. 4, 1995

[54] METHOD FOR PERFORMING A GASTRIC WRAP OF THE ESOPHAGUS FOR USE IN THE TREATMENT OF ESOPHAGEAL REFLUX

[75] Inventors: Michael R. Harrison, San Francisco; Russell W. Jennings, Pacifica; Alan W. Flake, San Francisco, all of Calif.

[73] Assignee: The Regents of the University of California, Oakland, Calif.

[21] Appl. No.: 12,113

[22] Filed: Feb. 1, 1993

[51] Int. Cl.⁶ .............................................. A61B 17/00
[52] U.S. Cl. .................... 606/139; 606/151; 227/175; 227/181; 227/19; 128/898
[58] Field of Search ............... 606/139, 142, 143, 148, 606/151, 152, 153; 128/898, 4; 227/175, 178, 179, 181, 19, 901

[56] References Cited

U.S. PATENT DOCUMENTS

| | | |
|---|---|---|
| 3,261,357 | 7/1966 | Roberts . |
| 3,551,987 | 1/1971 | Wilkinson . |
| 3,717,151 | 2/1973 | Collett . |
| 4,310,115 | 1/1982 | Inoue ..................................... 227/19 |
| 4,485,817 | 12/1984 | Swiggett . |
| 4,607,620 | 8/1986 | Storz . |
| 4,608,965 | 9/1986 | Anspach . |
| 4,635,638 | 1/1987 | Weintraub . |
| 4,655,219 | 4/1987 | Petruzzi . |
| 4,760,848 | 8/1988 | Hasson . |
| 4,763,668 | 8/1988 | Macek . |
| 4,773,420 | 9/1988 | Green ..................................... 227/19 |
| 4,784,137 | 11/1988 | Kulik . |
| 4,863,438 | 9/1989 | Gauderer . |
| 4,944,443 | 7/1990 | Oddsen et al. ....................... 227/19 |
| 4,944,732 | 7/1990 | Russo . |
| 4,944,741 | 7/1990 | Hasson . |
| 4,982,727 | 1/1991 | Sato . |
| 4,994,079 | 2/1991 | Genese . |
| 5,007,900 | 4/1991 | Picha . |
| 5,015,249 | 5/1991 | Nakao . |
| 5,035,248 | 7/1991 | Zinnecker . |
| 5,040,715 | 8/1991 | Green . |
| 5,042,707 | 8/1991 | Taheri . |
| 5,071,430 | 12/1991 | de Salis . |
| 5,073,166 | 12/1991 | Parks . |
| 5,088,979 | 2/1992 | Filipi et al. ........................... 604/26 |
| 5,099,827 | 3/1992 | Melzer et al. ...................... 606/142 |
| 5,104,394 | 4/1992 | Knoepfler ........................... 606/143 |
| 5,156,608 | 10/1992 | Trdidl et al. ....................... 606/142 |
| 5,197,649 | 3/1993 | Bessler et al. ...................... 227/19 |
| 5,207,691 | 5/1993 | Nardella ............................ 606/143 |
| 5,254,126 | 10/1993 | Filipi et al. ........................ 606/148 |

FOREIGN PATENT DOCUMENTS 1169625  7/1985  U.S.S.R. ............................ 606/153

OTHER PUBLICATIONS

Joel E. Richter, M.D., "Surgery For Reflux Disease–Reflections of a Gastroenterologist", in: The New England Journal of Medicine, vol. 326, No. 12, pp. 825–827.

Stuart Jon Spechler, M.D. et al; "Comparison Of Medical And Surgical Therapy For Complicated Gastroesophageal Reflux Disease In Veterans", in: The New England Journal Of Medicine; Mar. 19, 1992; pp. 786–792.

Primary Examiner—Stephen C. Pellegrino
Assistant Examiner—Jeffrey A. Schmidt
Attorney, Agent, or Firm—Townsend & Townsend Khourie & Crew

[57] ABSTRACT

The invention provides a method of fundoplication of the stomach to the esophagus comprising introducing an esophageal manipulator (72) into the stomach lumen (10), maneuvering the manipulator within the lumen so as to create an intussusception (48) of the esophagus (14) into the stomach, introducing a stapler (68) to the lumen of the stomach, and stapling the intussuscepted esophagus to the stomach operation of the stapler is from within the lumen of the stomach. The invention also provides a medical or surgical stapler comprising an elongated body (80) having a passageway (70) which is adapted to receive a medical component such as a forceps (72) or fluid.

10 Claims, 8 Drawing Sheets

METHOD FOR PERFORMING A GASTRIC WRAP OF THE ESOPHAGUS FOR USE IN THE TREATMENT OF ESOPHAGEAL REFLUX

BACKGROUND OF THE INVENTION

Gastroesophageal reflux (GER) is a major problem with serious consequences in both the pediatric and adult population. GER includes reflux or regurgitation of stomach contents up into the esophagus. Occasionally the stomach contents, including acids, are aspirated into the pulmonary tree. GER is especially serious in infants, but many adults are also troubled with the symptoms. Frequent complications include esophagitis and esophageal stricture, intractable vomiting, asthma, and aspiration pneumonia. In infants and children GER has been associated with a wide spectrum of symptoms including vomiting, failure to thrive, recurrent aspiration pneumonia, apnea, sudden infant death syndrome, and brain damage. There is also a high incidence of GER in patients who have undergone correction of esophageal atresia or abnormal esophageal narrowing.

The gastroesophageal junction (GEJ) is an anatomical region including the junction of the stomach and esophagus. The GEJ combined with the lower esophageal sphincter (LES) forms a valve between the stomach and esophagus. The LES is formed of circular bands of muscle at the distal esophagus near the stomach. Incompetence of the valve contributes to symptoms of GER. In the last three decades improved understanding of the pathophysiology of GER has led to development of a variety of surgical procedures designed to construct a competent valve at the GEJ. Although usually effective, all are associated with significant morbidity and the risk of recurrence.

Figure 1A:
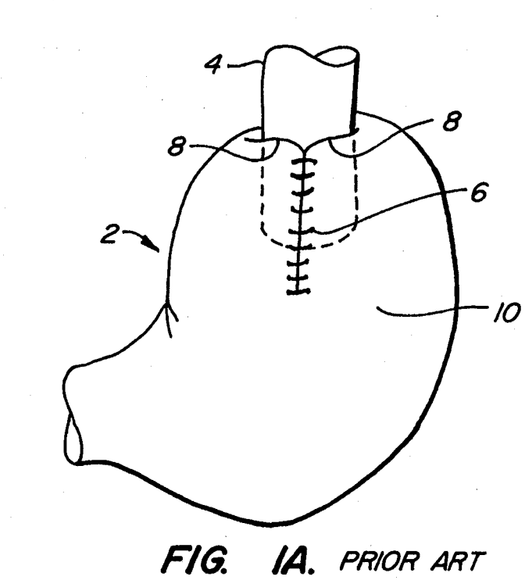
FIG. 1A is a schematic showing a prior art fundoplication.

Fundoplication is a surgical treatment for GER. This corrective surgery typically involves a major operation with a large incision to expose the stomach and lower esophagus. Without penetrating the stomach, the esophagus is pulled down below the hole in the diaphragm through which the esophagus is normally admitted. Then a portion of the stomach, the fundus, is plicated or gathered up and wrapped around the distal end of the esophagus and sewn in place from the outside of the stomach and esophagus. FIG. 1a is a schematic of a conventional fundoplication of a stomach 2 to an esophagus 4. Suture line 6 represents surgical fixation of folds 8 to create the fundoplication. Folds 8 are in the fundal region of stomach 2. Folding the fundus up and around the distal end of esophagus 4 forms the fundoplication. The stomach lumen 10 is not entered. Suture line 6 holds folds 8 in place; it does not represent repair of a gastric incision.

Some current anti-reflux procedures are the Nissen, Thal, and Belsey. All these procedures require an abdominal or thoracic incision to wrap the stomach around the esophagus. The Belsey can require surgical removal of part of a rib. Each procedure takes about two hours to perform and they are attended by significant morbidity and mortality. In addition to being lengthy surgical procedures, spontaneous undoing of the plication is a major problem. Slippage has been the major cause of operative failures.

The most commonly performed operation for correction of GER in infants and children has been the Nissen fundoplication. The Nissen is associated with postoperative complications of small bowel obstruction, paraesophageal hernia, wrap slippage, and the gas-bloat syndrome. Although another procedure, Thal fundoplication, appears to have fewer postoperative complications, it has not been as widely used due to a higher rate of recurrent GER.

Successful techniques for the surgical treatment of gastroesophageal reflux appear to have several features in common: 1) lengthening of the indraabdominal portion of esophagus, 2) decreasing the angle of His, 3) construction of a valve mechanism at the GEJ, and 4) forming a complete or partial gastric wrap around the esophagus to augment extra-esophageal pressure (pressure originating outside the esophagus and acting on the esophagus). Recent technical advances in endoscopic surgery allow performance of a growing number of operations a minimally invasive manner.

Figure 1B:
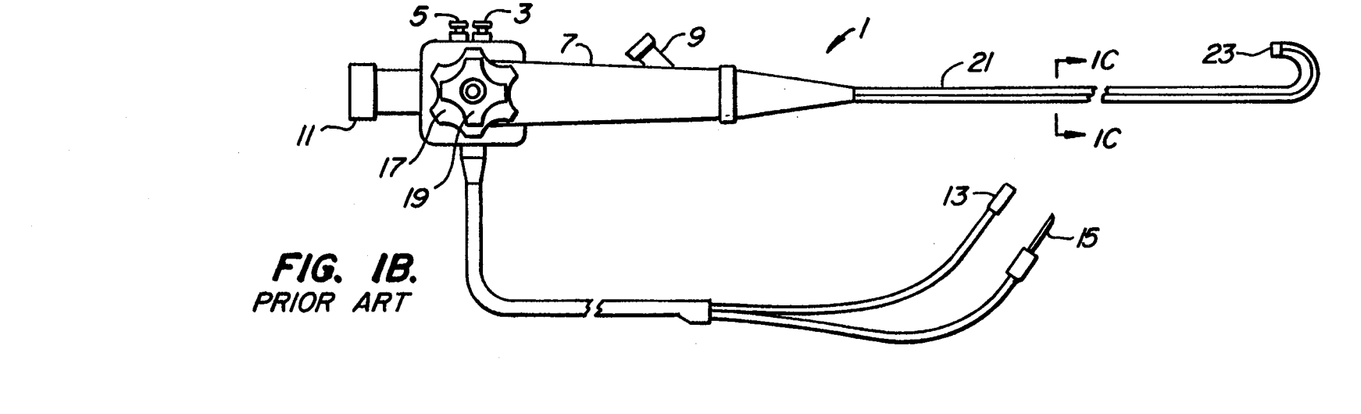
FIG. 1B is a schematic showing a prior art flexible endoscope.
Figure 1C:
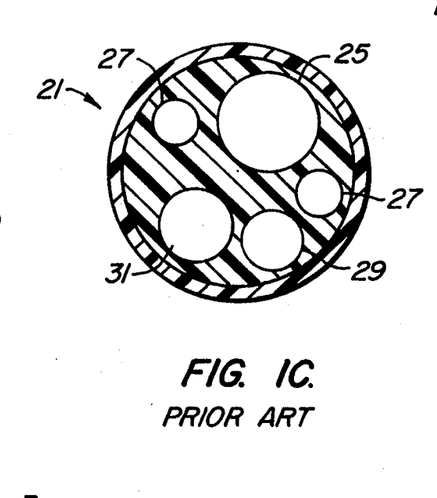
FIG. 1C is a schematic showing a cross section of a prior art flexible endoscope taken through the insertion tube.

A schematic of a conventional flexible endoscope 1 is shown in FIG. 1B and a cross-sectional area of its insertion tube 21 is shown in FIG. 1C. Endoscope 1 typically includes a depressible button 3 to control air and water influx, a control 5 to manipulate suction, and a control head 7. A biopsy channel inlet 9 is typically located on control head 7, as is an eye piece or viewing aperture 11. Endoscope 1 communicates with an external air and/or suction device through end 13 and to an external light source through end 15. Knob 17 controls up and down deflection of a flexible tip 23 at the distal end of insertion tube 21 and knob 19 controls left/right deflection of tip 23. A cross-sectional view of insertion tube 21 includes a lens 25, a light source 27, an air and water channel 29, and a biopsy and suction channel 31.

In use, the operator inserts distal tip 23 down the esophagus of an anesthetized patient and into the patient's stomach. The operator can manipulate control knobs 17 and 19 to view an area of interest. Air and water can be injected into the patient's stomach to assist in viewing an area clearly. Air, water and other fluids can be removed by use of the suction. The availability of flexible fiberoptic endoscopes has facilitated the development of new surgical procedures and approaches.

SUMMARY OF THE INVENTION

The invention provides a method of fundoplication of a patient's stomach to his esophagus. Steps of the method include introducing an esophageal manipulator into the stomach lumen, maneuvering the manipulator within the lumen so as to create an intussusception of the esophagus into the stomach, introducing a tissue securing device to the lumen, and securing the intussuscepted esophagus to the stomach using the securing device and operating from within the lumen of the stomach. The securing device is preferably a stapler. The esophageal manipulator can be any of a variety of instruments, such as a hook, forceps, clamp, or other device adapted to grasp, control, engage or otherwise direct the esophageal or gastric tissue.

"Intussusception" means that a part of the lumen of a hollow viscera or tubular structure is received by the lumen of an immediately adjoining part. "Lumen" generally refers to the interior of a hollow or potentially hollow structure such as a tubular structure. "Plication" means tucking or folding with the effect of shortening the plicated structure. "Fundoplication" means plication of the fundus of the stomach up around the lower or distal end of the esophagus which has been mobilized.

A preferred method includes performing a percutaneous endoscopic gastrostomy (PEG). At least one of the esophageal manipulator and the tissue securing device is introduced to the stomach lumen through the gastrotomy incision. The securing device, such as a stapler, can have a longitudinally extending passageway through which the esophageal manipulator is passed for introduction into the lumen. Most preferably, endoscopic guidance assists with positioning at least one of the esophageal manipulator and the securing device. If the securing device is a stapler, it can emit staples in a variety of patterns. A T-shaped pattern is preferred. The staples are preferably positioned substantially perpendicular to a long axis of the esophagus.

The invention provides a method of fundoplication of a patient's stomach to his esophagus comprising the steps of creating an incision in the patient's abdomen, approaching the stomach wall of the patient through the abdominal wall incision, incising the stomach wall, introducing an esophageal manipulator into the stomach lumen, engaging esophageal tissue by the manipulator, maneuvering the manipulator so as to create an intussusception of the esophagus into the stomach, introducing a tissue securing device, such as a stapler, to the lumen of the stomach, and securing the intussuscepted esophagus to the stomach.

The method of the invention can further include the step of introducing a hollow visceral access port through the abdominal incision and the stomach wall incision into the stomach lumen. The access port car include a resorbable tubular sheath.

The invention also includes a method of plication of a viscus other than the stomach and esophagus. An example is plication of the urethra to the urinary bladder. This method comprises introducing a tissue manipulator into a lumen of the viscus (such as the bladder), maneuvering the manipulator so as to create an intussusception of a proximate structure (such as the urethra) into the viscus, introducing a tissue securing device to the lumen of the viscus, and securing the intussuscepted viscus to the proximate structure. The securing device is preferably a stapler. The tissue manipulator can be any of a variety of instruments, such as a hook, forceps, clamp, or other device adapted to grasp, control, engage or otherwise direct tissue.

The invention further includes a novel stapler adapted to staple tissue and for medical or surgical use with a medical component. The stapler has an elongated body having a first or proximal end and a second or distal end and a passageway extending therebetween. The passageway is adapted to house the medical component along the passageway. The stapler has a stapler head, positioned towards the first end, adapted to staple the tissue, and an actuator, positioned towards the second end and operatively coupled to the stapler head, adapted to actuate the stapler head so as to staple the tissue.

The medical component received by the passageway can be any of a number of items useful in medical or surgical procedures. Examples include an esophageal manipulator, a tissue manipulator, a fluid including gases and liquids, reagents and medication. Most preferably, the passageway is adapted to receive a tissue engaging apparatus such as a grasping forceps, a biopsy forceps, a clamp, and a hook.

The stapler head can have a hinged jaw adapted to contact tissue and expel staples therein, and the actuator preferably includes a hand grip. The stapler head can be adapted to simultaneously drive a plurality of the staples into the tissue in a T-shaped pattern. The individual staples are preferably longer than they are wide and are oriented with the length substantially perpendicular to an arm of the T-shaped pattern. Most preferably, the stapler is dimensioned and adapted for admittance into a channel within an endoscope.

The stapler is particularly useful for fundoplication of the patient's stomach to the esophagus from the interior of the stomach. Preferably, the tissue engaging apparatus is used to grasp the tissue to be stapled and pulls the tissue into the region between the jaws of the stapler. The jaws are snapped shut onto the tissue to drive the staples into the grasped tissue. The jaws and tissue engaging apparatus then release the stapled tissue. The process can be repeated at different axial and rotary positions until the desired fundoplication is achieved.

Other features and advantages of the invention will appear from the following description taken together with the accompanying drawings.

BRIEF DESCRIPTION OF THE DRAWINGS

FIGS. 8A, 8B, 8C and 8D show details of a stapler having movable jaws and a passageway which admits a grasping device.

DESCRIPTION OF THE PREFERRED EMBODIMENT

The invention includes two primary aspects: (1) the grabbing and retraction of esophageal tissue for creation of an intussusception at the GEJ accomplished from within the lumen of the stomach; and (2) a specialized staple gun which preferably accepts an axially moveable retraction device and has a particular pattern of staples.

The invention was tested in pigs because the pig is an established model for gastroesophageal reflux investigation. The following protocol was approved by the University of California San Francisco Committee on Animal Research. Six York-Hampshire pigs were obtained from Pork Power (Tracy, Calif.).

The pigs were fasted for two days except for unrestricted access to water until 12 hours prior to the experiment. They were immobilized with intramuscular ketamine (10 mg/kg). Inhalational anesthesia with 1-2% isoflurane and oxygen was given by endotracheal tube and mechanical ventilation (Narkovet Ill., North American Drager, Telford, Pa.). Subjects were placed on 5 centimeters (cm) water positive end expiratory pressure (PEEP) with tidal volume and rate adjusted to maintain normal oxygen saturation without overbreathing. Subjects were kept warm with a circulating water blanket. A volume of 500 milliliters (ml) of normal saline was infused intravascularly during the operation to maintain hydration.

Figure 3:
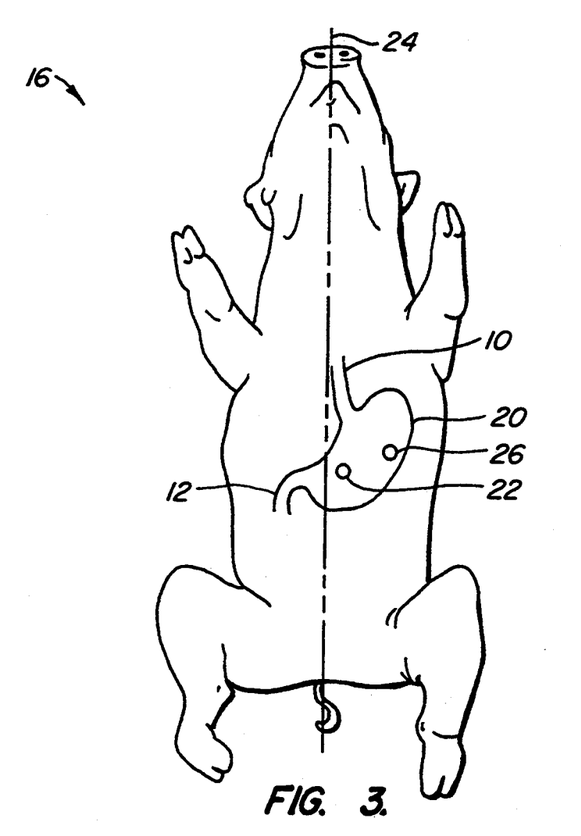
FIG. 3 shows placement of endoscopic ports in the porcine model of gastroesophageal reflux.

Subjects were placed on the operating table in the supine position. The table was tilted into 20 degrees reverse Trendelenburg. A flexible pediatric gastroscope 18 was placed into the lumen 32 of stomach 20 of subject 16 and angled anteriorly to transilluminate a site for a medial endoscopic port 22. See FIG. 3. A medial gastrotomy incision was placed in direct line with esophagus 24, about 2 cm to the right of the xyphoid and as far inferiorly as possible. A lateral gastrostomy incision was placed in the left anterior axillary line as far inferiorly as possible in preparation for receipt of a lateral port 26.

Figure 4:
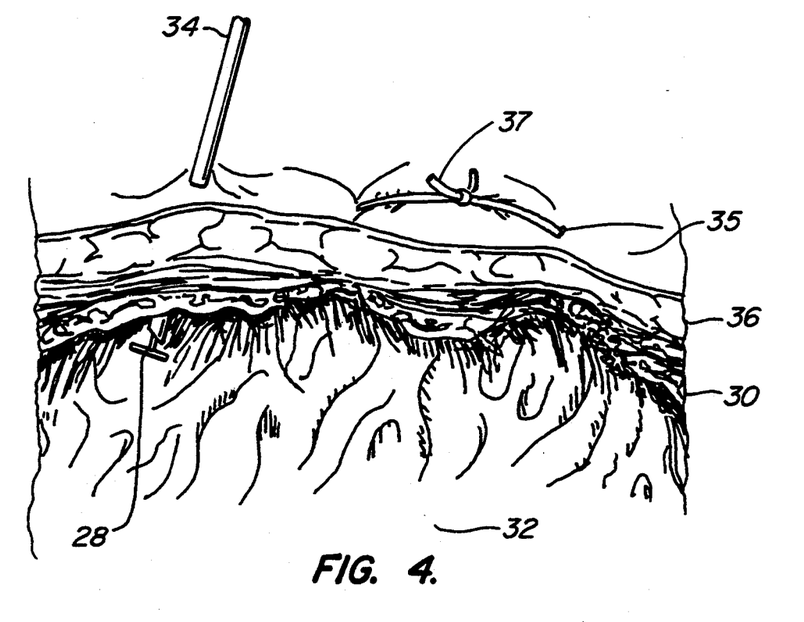
FIG. 4 shows gastrostomy details of the porcine model.

The technique involved construction of a gastrostomy with nylon T-bar fixation devices 28 to provide positive control of the gastric or stomach wall 30. See FIG. 4. Stomach 20 was insufflated to 15 cm water pressure and a trocar 34 was inserted through the skin 35 and the abdominal wall 36 into stomach 20. T-bar 28, in flexed or collapsed position, was passed through trocar 34 and allowed to open inside lumen 32 of stomach 20. The position was confirmed with gastroscope 18. After all 8 T-bars were inserted, they were tied together with suture 37 in pairs to provide fixation of stomach wall 30 to abdominal wall 36. This process was the same for both the medial and lateral incisions.

Through each gastrostomy, a 12 millimeter (mm) endoscopic port, 22 and 26, was placed into stomach 20. A 10 mm rigid (0° flexion) endoscope (Karl Storz, Germany), not shown, was passed through one of the ports to provide visualization of the gastroesophageal junction (GEJ) 38 and flexible scope 18 was withdrawn.

Figure 5:
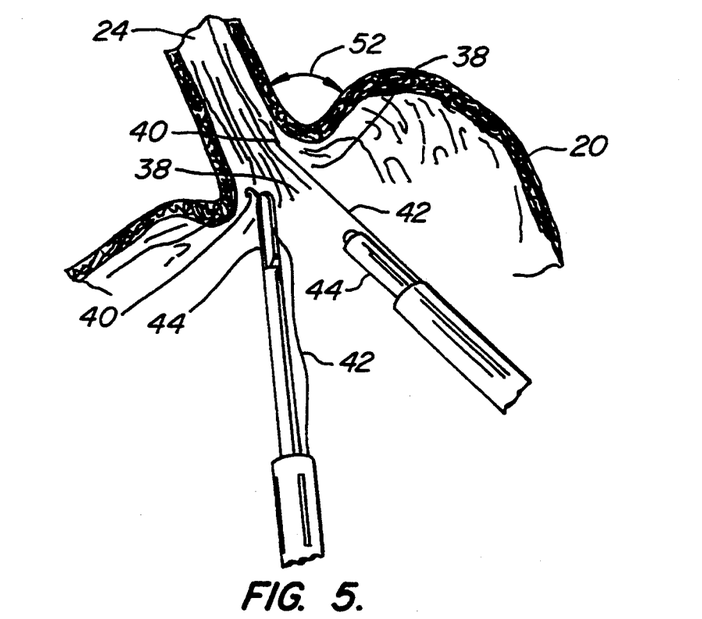
FIG. 5 shows hook placement in the porcine model.

After entering stomach 20, the GEJ 38 was identified. Fixation of GEJ 38 for placement of staple lines was achieved by internal traction with endoscopic hooks 40. See FIG. 5. Each small hook 40 on a suture 42 was passed through endoscopic ports 22/26, alternating with the position of the rigid scope (not shown). Hooks 40 were placed into GEJ 38 under direct vision using endoscopic graspers 44. A pair of graspers 44 was used to position each hook 40 in the GEJ 38, and tension was applied through the endoscopic ports 22/26 to pull GEJ 38 into stomach 20.

Figure 6:
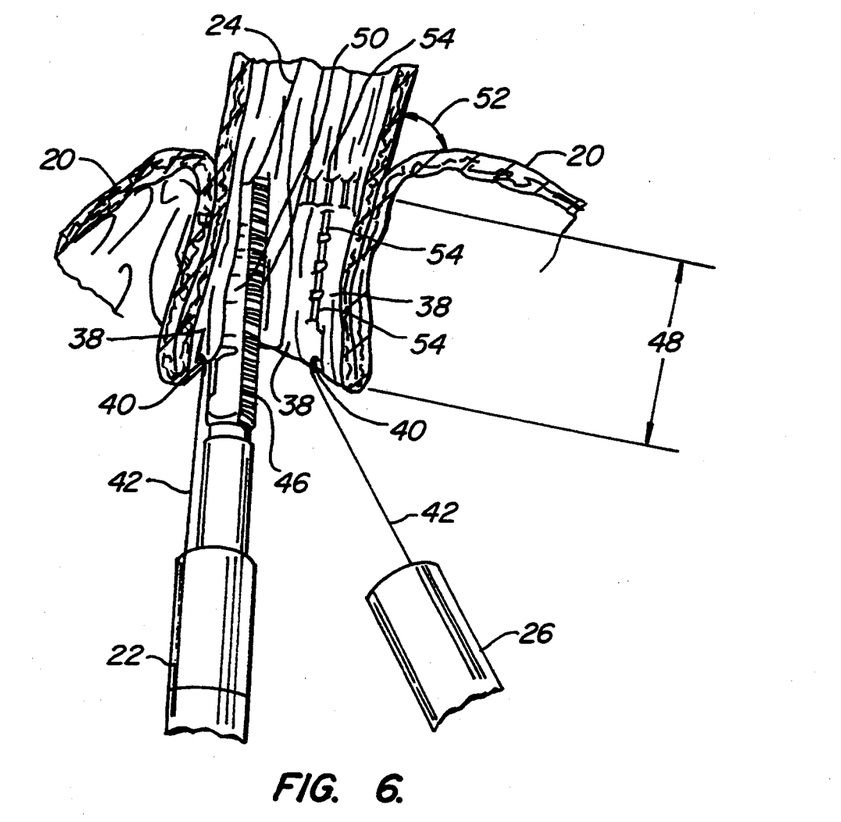
FIG. 6 shows a stapling detail in the porcine model.
Figure 7A:
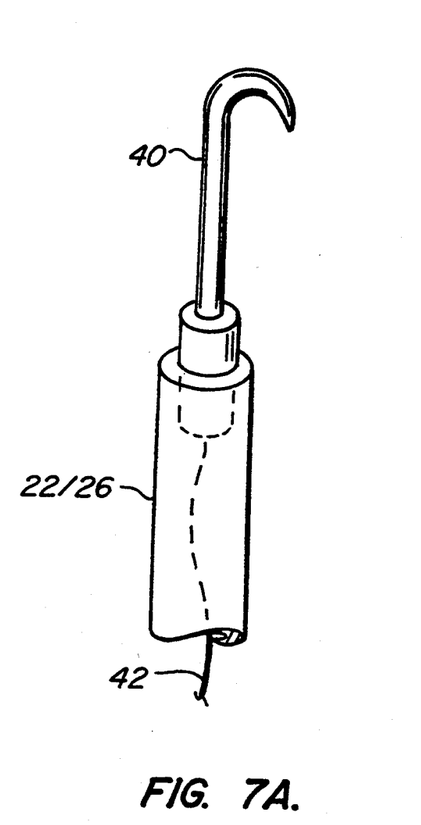
FIGS. 7A and 7B show details of a tethered hook device.
Figure 7B:
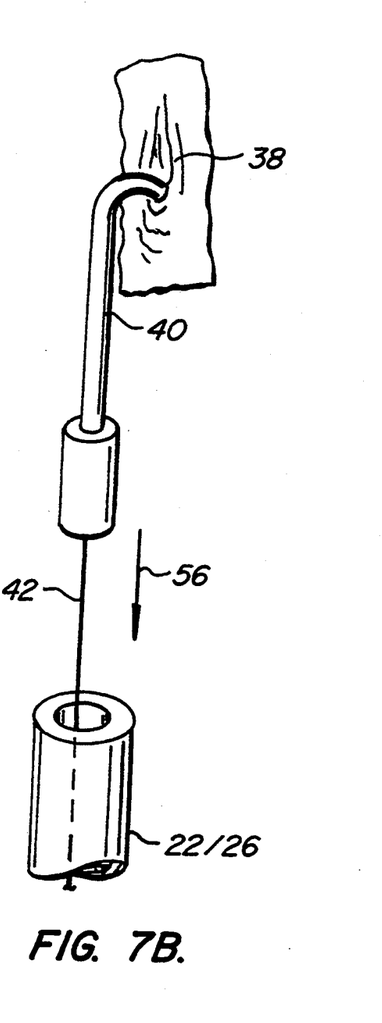

A GIA is a commercially available endoscopic accessory for cutting and stapling in one step. A modified 4.7 mm Endo GIA 30 (U.S. Surgical, Norwalk, Conn.) with the knife removed was introduced (46). See FIG. 6. In the open position, one jaw 50 of GIA stapler 46 was passed down esophagus 24 while the other jaw was pushed against stomach 20, while tension was applied to traction hooks 40. See FIG. 7B. Arrow 56 shows the direction of applied tension. The effect was to pull GEJ 38 into the stapler jaws while creating an intussusception 48. Stapler 46 was fired to fix stomach 20 to esophagus 24 in the intussuscepted position. This process was repeated 3 times, one row each in the right anterior, the right posterior, and the left lateral position to decrease the angle of His 52. Staples 54 preferably form a T-pattern.

During each experiment, GEJ 38 was tested for reflux. A nasogastric tube with a pH probe attached was placed into stomach 20, documenting the level of GEJ 38 as the point of drop in pH and return of gastric contents. A volume of 10 ml/kg of 0.1 normal hydrochloric acid (N HCL) was instilled into stomach 20. The pH probe and the nasogastric tube were pulled back 5 cm above GEJ 38. A series of tests of gastroesophageal reflux were done; 5 minutes with the animal supine, 5 minutes with a 10 kg weight on its abdomen, and 5 minutes in Trendelenburg position of 30 degrees. Continuously recorded esophageal pH documented any gastric acid reflux into the esophagus. The animals were sacrificed after these tests.

The endoscopic antireflux procedure was easily performed. Creation of the two gastrostomies was the most time consuming part of the procedure. The gastrostomies were useful for placement of ports 22/26 and easily withstood the multiple insertions of instruments required for the procedure, providing secure, leak free gastric access.

The use of small endoscopic hooks 40 placed endoscopically allowed traction on GEJ 38 which then intussuscepted 48 into stomach 20. Once this step was performed, fixation of esophagus 24 in the intussuscepted intragastric position was done. The size of hooks 40 was important: if they were too large they tended to perforate esophagus 24, and if too small they grabbed only esophageal mucosa which easily tore. Preferably, a diameter of hook 40 is about 5 mm.

Placement of three rows of staples with endoscopic stapler 46 was easily performed and fixed esophagus 24 in the intragastric position. There was no gastric or esophageal leakage despite the through-and-through placement of staples 54.

When the completed antireflux procedure was tested for competence, it prevented acid reflux into the esophagus after acid instillation into the stomach. The endoscopic transgastric antireflux procedure prevented gastric acid reflux during performance of maneuvers designed to elicit GER such as abdominal compression and Trendelenburg position. Autopsy revealed formation of a flap valve at GEJ 38 with intussusception 48 of esophagus 24 into stomach 20. The flap valve collapses inwardly due to intragastric pressure.

The invention is preferably practiced clinically as follows: An endoscope 58 is placed down esophagus 14 into stomach lumen 10 while the patient is under general anesthesia. Stomach lumen 10 is inflated with air. By correctly positioning endoscope 58, the stomach wall 78 can be directed towards the abdominal wall (not shown). The surgeon makes an incision in the skin to enter stomach lumen 10 through the abdominal wall. Alternatively, a needle is inserted into stomach 10 through the abdominal wall and a wire is placed along the needle's path. A dilator is placed over the wire to enlarge the opening which will become the gastrostomy. This procedure with modifications is well known and is called a Percutaneous Endoscopic Gastrotomy or PEG.

Figure 8A:
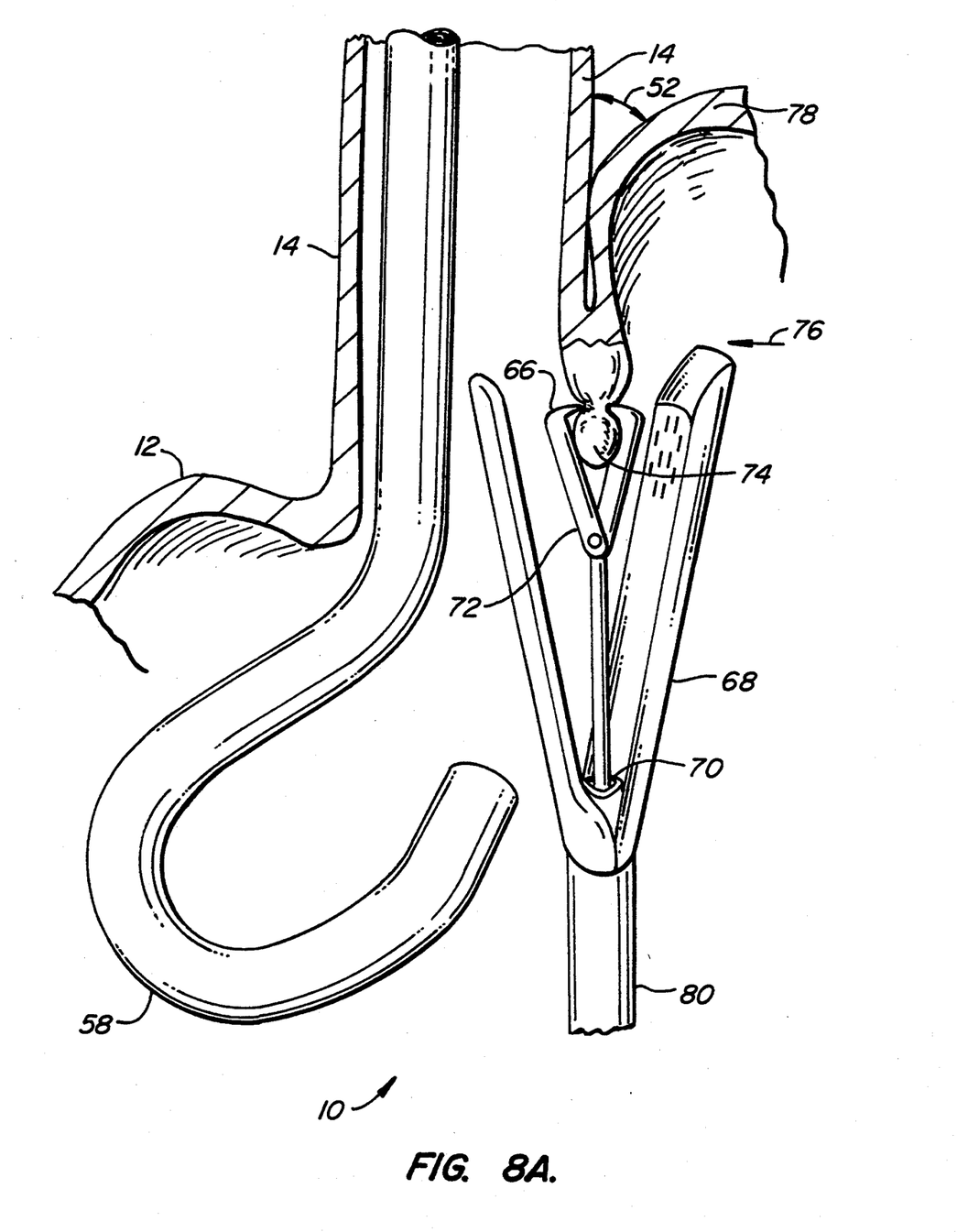
FIG. 8A shows a stapler grasping tissue at the GEJ with endoscopic guidance.

At least one hook device such as a tethered hook 40 (FIG. 7A) or a device to grab tissue, such as a device with a moveable jaws 66 (FIG. 8A), is introduced through the port. Tethered hook 40 preferably has a diameter of about 5 mm. Hook 40 is attached to a line such a suture material 42. Thus, tension (shown by arrow 56) on suture 42 is transmitted to hook 40. See FIG. 7B. With endoscopic guidance, device 40 or 66 grabs tissue at the GEJ. See FIG. 8A. This gastroesophageal tissue is pulled downward into stomach lumen 10, creating an intussusception of esophagus 14 into stomach lumen 10. The intussuscepted esophagus 14 is stapled to the wall of gastric fundus 78 to create a fundoplication.

A port, not shown, is placed to gain access from the skin surface to the stomach lumen. Such ports are known and used for PEG procedures. See, for example, U.S. Pat. Nos. 4,863,438; 4,944,732; and 5,007,900 which are incorporated by reference herein. The port could include a resorbable sheath so that surgical removal of the port is unnecessary.

Alternatively, using gastroscope 58 for visualization, an instrument is passed through the port and sutures (not shown) are applied through the GEJ. These sutures are used for maintaining tension on the GEJ and pulling the GEJ down into the abdomen. When this is done, the esophagus is intussuscepted into the gastric fundus. Using gastroscope 58 for visualization, the tension sutures are pulled out through the instrument port. Tension is maintained on these sutures as instruments are passed in.

Figure 2:
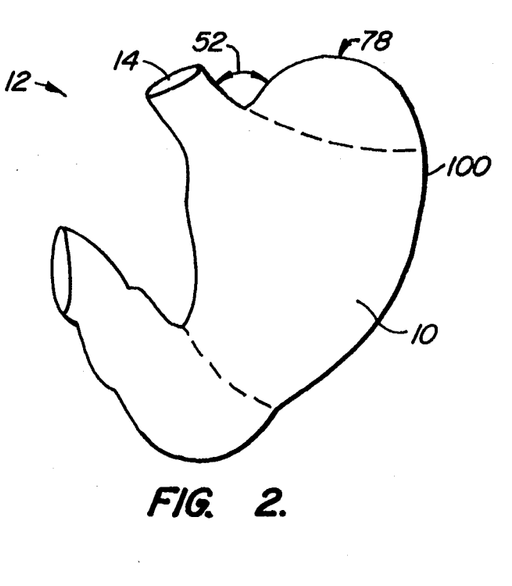
FIG. 2 is a schematic of a human stomach.
Figure 8B:
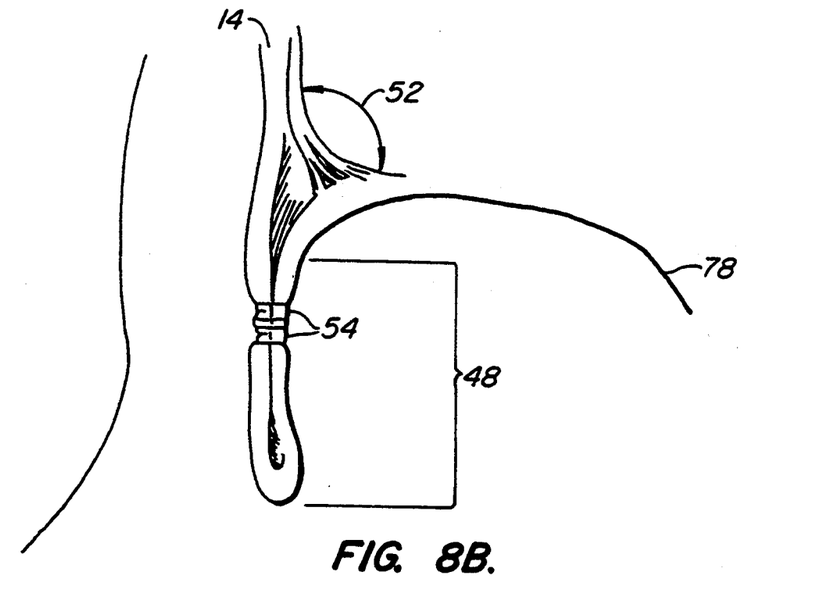
FIG. 8B shows tissue stapled by the device of FIG. 8A.

The invention uses a stapling device 68 to fix fundal wall 78 alongside the esophagus 14 to form an esophageal wrap from within stomach lumen 10. See FIG. 8A. See FIG. 2 generally for anatomic references to the stomach. FIG. 8B shows staples 54 placed to secure intussusception 48 of esophagus 14 to fundus 78. The angle of His 52 becomes more acute after the stapling procedure. An advantage is that the method can be done with minimum invasion by use of endoscopic techniques. It also provides an esophageal wrap that can be done in a very short period of time, preferably about 15 minutes. This should lead to reduced morbidity and mortality. In addition, because of the vertical staples, the wrap is less likely to slip.

Figure 8C:
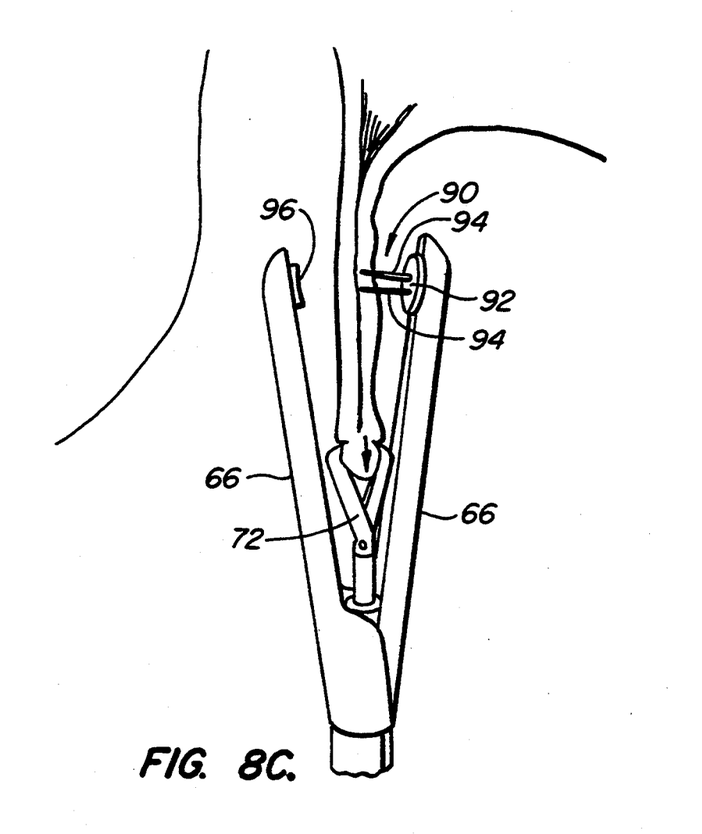
FIG. 8C shows an alternative stapler emitting a tack.

Stapler 68 is preferably a specialized modification of existing staple guns, such as those made by Ethicon Autosuture GIA of Cincinnati, Ohio, or U.S. Surgical Endo GIA of Norwalk, Conn. See FIGS. 8A and 8C for details of the stapling end of stapler 68. See FIG. 9 for a schematic of the entire stapler 68, including its internal grasper 72. Stapler 68 includes a passageway 70 through which hook 40 or jaw-like grasper 72 is introduce so that a single step accomplishes grabbing of esophageal tissue and stapling. The staples should be oriented horizontally, although the procedure works with vertically oriented staples. "Horizontal" in this context means perpendicular to a long axis of the esophagus. That is, the axially extending body of the staple is horizontal in contrast to the radially extending legs of the staple. Vertically oriented staples are depicted because the stapler used was a modified prior art device. Preferably the staples form a T configuration and the tip 74 of the plicated fundus and esophagus is left unstapled and floppy to assist in functioning as a valve. See FIG. 10 for a detail of a stapler jaw designed to emit staples in a T-shaped pattern.

Staplers can be designed specifically for the invention. A stapling device which performs the dual tasks of traction on the GEJ and placement of a T shaped staple line above the GEJ is preferred. This device incorporates either a central grasping device or aligned grasping devices on either side of the stapler. The GEJ is grasped, traction applied to pull the GEJ into the jaws of the Stapler to the appropriate depth, and the stapler is fired.

Figure 9:
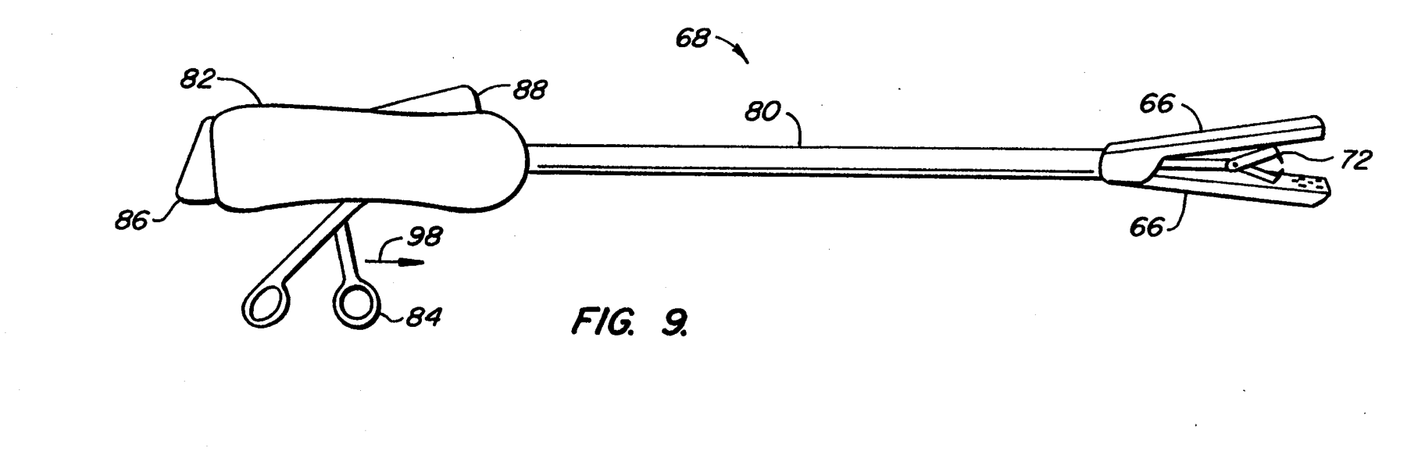
FIG. 9 is a schematic of the entire stapler with a grasping device.
Figure 10:
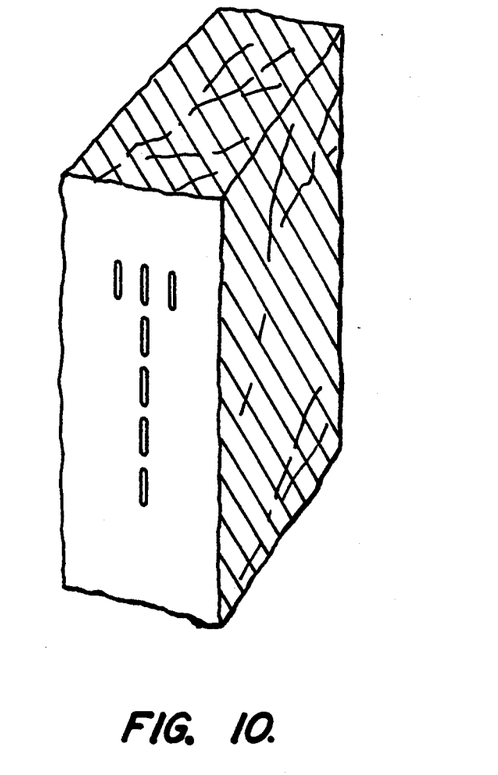
FIG. 10 is a detail of stapler jaw 66 showing a T-shaped pattern for emitting staples.

A schematic of the entire stapler device 68 is shown in FIG. 9. At an operating end are movable jaws 66. These are connected by means of elongate body 80 to a handle 82. Elongate body 80 includes a passageway which can house grasper 72. Grasper 72 is independently movable within body 80 by means of movable handle 84 as indicated by arrow 98. Also included is a button 86 on handle 82 which tightens stapler jaws 66. Button 88 on handle 82 fires the staples from the operating end of jaws 66.

Alternatively, a tissue approximator (TA) stapler is admitted. One jaw is placed inside the esophagus, the other along the gastric wall to be placed next to a tension suture. The TA is pushed up thus approximating the gastric wall to the esophagus and the TA is fired. The preferred length of the endoscopic TA stapler head is 3 cm. Modifications of the stapling device may be desirable, including placing the traction sutures through a small opening in the stapler and allowing the stapler to slide up the suture much as a dilator goes along a wire. This would insure very accurate placement on the GEJ where the suture is placed.

Figure 8D:
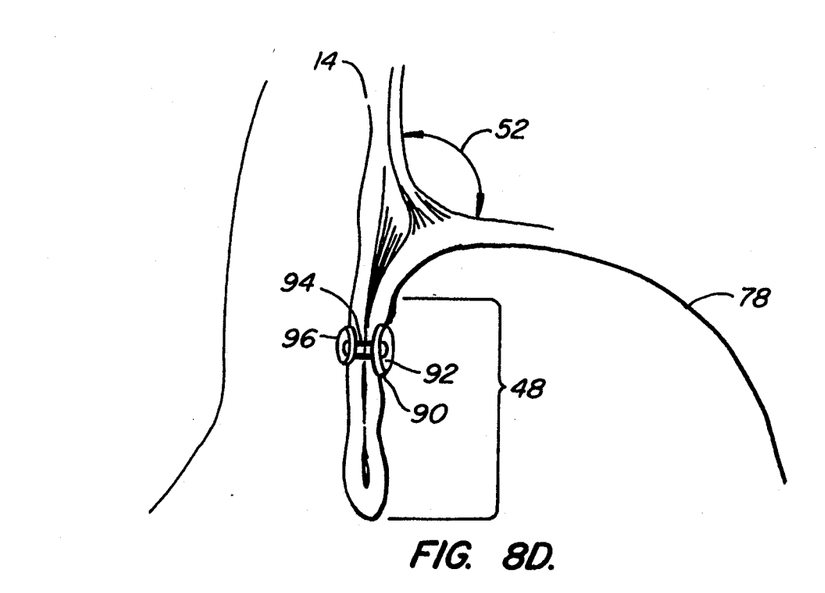
FIG. 8D shows tissue after stapling by the device of FIG. 8C.

Instead of conventional surgical staples, tacks could be fired by the stapler. See FIGS. 8C and 8D. Movable jaws 66 can be adapted to hold a tack 90. Preferably, tack 90 includes a head 92, two legs 94, and is secured by a foot 96 after firing of stapler 68. FIG. 8D shows a tack 90 which has been secured in place to hold intussusception 48 of esophagus 14 to fundal wall 78. Angle of His 52 is more acute than preoperatively.

In any of the embodiments of the invention, lengthening of the intraabdominal esophagus can be achieved without dividing the phrenoesophagal ligament and mobilizing the GEJ as is done in open procedures. This is accomplished not by pulling the esophagus down into the abdomen as in open fundoplication procedures but rather by pushing the diaphragm and stomach up around the esophagus and fixing them in place. The net effect is equivalent: the esophagus is surrounded by intraabdominal pressure instead of negative intrathoracic pressure, but the integrity of the GEJ is not disrupted.

The formation of a gastric wrap around the esophagus is an important element in preventing esophagal reflux because intragastric pressure is applied to the outside of the esophagus. Thus, increased intragastric pressure should not overcome the lower esophageal sphincter pressure. This technique forms a gastric fundoplication similar to the Belsey Mark IV.

The angle of His 52 is decreased by placing the staple line along greater curvature 100. See FIG. 2. The effect is to fold stomach 12 up alongside esophagus 14. This creates a type of flap valve that tends to close the lower esophageal sphincter in the direction of arrow 76. See FIG. 8A. The flap valve is preferably a 3 cm length of esophagus 14 which is intussuscepted into stomach 12. Following the principles of Kock valve creation, a technique known and used to surgically correct uterine prolapse, this forms an antireflux valve.

In addition to satisfying the anatomic requirements of an antireflux procedure, the inventive approach has other advantages. The gastric fundoplication is performed without entering the peritoneal cavity. Absence of intraperitoneal invasion decreases or eliminates the risk of adhesion formation and subsequent small bowel obstruction, a particularly dangerous complication of adhesions. A second advantage is most apparent in the high risk group of neurologically damaged children.

The minimally invasive nature of the inventive technique decreases surgical morbidity in this compromised population. Also performance of an antireflux procedure at the time of gastrostomy in the absence of documented reflux would be uncontroversial with the use of a minimally invasive procedure with low morbidity.

Although the invention has been described in detail, the artisan will appreciate that there are other modifications which would not depart from the invention. For example, instead of placing the stapler through the operating port in the stomach, a reversed stapler with the jaws facing backwards could be passed down the esophagus using visualization through the esophagus or the gastrostomy port. Retraction sutures would maintain traction as the stapler is pulled back up the esophagus with one jaw projecting into the stomach. This would provide the same maneuver as the TA description above. Also, a securing device other than a stapler could be used. For example, instruments competent to assist in placing sutures could be employed instead of a stapler. Thus, the invention is not limited by the preceding description and the illustrations, but rather by the appended claims.

What is claimed is:

1. A method of fundoplication of a stomach to an esophagus of a patient comprising:
    a. introducing an esophageal manipulator through a percutaneous endoscopic gastrostomy and into a lumen of the stomach;
    b. maneuvering the manipulator within the lumen so as to create an intussusception of the esophagus into the stomach;
    c. introducing a tissue securing device to the lumen of the stomach; and
    d. securing the intussuscepted esophagus to the stomach using the tissue securing device operating from within the lumen of the stomach.

2. The method of claim 1 further comprising the step of using endoscopic guidance to assist with positioning of at least one of the esophageal manipulator and the tissue securing device.

3. The method of claim 1 wherein the tissue securing device is a stapler.

4. The method of claim 1 wherein the tissue securing device introducing step is carried out using a stapler having a longitudinally extending passageway, and further comprising the step of introducing the esophageal manipulator through said passageway in the stapler.

5. The method of claim 4 further comprising the step of arranging the staples in a T-shaped pattern.

6. The method of claim 4 further comprising the step of positioning the staples substantially parallel to a long axis of the esophagus.

7. A method of plication of a viscus of a patient comprising:
    a. making an incision in the wall of the viscus;
    b. introducing a tissue manipulator through the incision and into a lumen of the viscus;
    c. maneuvering the manipulator so as to create an intussusception of a proximate structure into the viscus;
    d. introducing a tissue securing device to the lumen of the viscus; and
    e. securing the intussuscepted viscus to the proximate structure.

8. The method of claim 7 wherein the tissue securing device is a stapler.

9. A method of fundoplication of a stomach to an esophagus of a patient comprising:
    a. creating a first incision in an abdomen of the patient;
    b. approaching the stomach wall of the patient through the abdominal wall incision;
    c. creating a second incision in the stomach wall of the patient;
    d. introducing through the first and second incisions and into a lumen of the stomach an esophageal manipulator;
    e. engaging esophageal tissue by the manipulator;
    f. maneuvering the manipulator so as to create an intussusception of the esophagus into the stomach;
    g. introducing a stapler to the lumen of the stomach; and
    h. stapling the intussuscepted esophagus to the stomach.

10. A method of fundoplication of a stomach to an esophagus of a patient comprising:
    a. introducing an esophageal manipulator into a lumen of the stomach;
    b. maneuvering the manipulator within the lumen so as to create an intussusception of the esophagus into the stomach;
    c. introducing a stapler, having a longitudinally extending passageway, to the lumen of the stomach;
    d. introducing the esophageal manipulator through said passageway in the stapler; and
    e. stapling the intussuscepted esophagus to the stomach using the stapler operating from within the lumen of the stomach.

* * * * *